United States Patent
Luchini et al.

(10) Patent No.: US 7,820,842 B2
(45) Date of Patent: Oct. 26, 2010

(54) POLYUNSATURATED FATTY ACID MONOVALENT AND DIVALENT METAL SALT SYNTHESIS

(75) Inventors: Daniel Nestor Luchini, Naperville, IL (US); George K. Strohmaier, Richfield, OH (US); Eiler D. Frederiksen, Henderson, NV (US); James G. Hawkes, Chicago, IL (US); Bob J. Dull, O'Fallon, IL (US)

(73) Assignee: Virtus Nutrition LLC, Turlock, CA (US)

( * ) Notice: Subject to any disclaimer, the term of this patent is extended or adjusted under 35 U.S.C. 154(b) by 435 days.

(21) Appl. No.: 10/598,681

(22) PCT Filed: Apr. 29, 2005

(86) PCT No.: PCT/US2005/014884

§ 371 (c)(1),
(2), (4) Date: Jun. 17, 2008

(87) PCT Pub. No.: WO2005/108535

PCT Pub. Date: Nov. 17, 2005

(65) Prior Publication Data

US 2009/0105335 A1    Apr. 23, 2009

Related U.S. Application Data

(63) Continuation-in-part of application No. 10/716,292, filed on Nov. 18, 2003, now Pat. No. 7,098,352, which is a continuation-in-part of application No. 10/299,337, filed on Nov. 18, 2002, now abandoned.

(60) Provisional application No. 60/566,972, filed on Apr. 30, 2004, provisional application No. 60/334,471, filed on Nov. 16, 2001.

(51) Int. Cl.
 *C07C 51/00* (2006.01)

(52) U.S. Cl. ................................. 554/156; 426/807
(58) Field of Classification Search ............ 554/156; 426/807
See application file for complete search history.

(56) References Cited

U.S. PATENT DOCUMENTS 3,959,493 A    5/1976 Baalsrud et al.
(Continued)

FOREIGN PATENT DOCUMENTS

EP    0 387 023 A1    9/1990
(Continued)

OTHER PUBLICATIONS

Formo et al., "Soap," Bailey's Industrial Oil and Fat Products, 4.sup.th ed., vol. 1, pp. 511-529 (1979).
(Continued)

*Primary Examiner*—Deborah D Carr
(74) *Attorney, Agent, or Firm*—Fox Rothschild LLP

(57) ABSTRACT

Disclosed herein are methods for the preparation of a free-flowing, storage-stable fatty acid metal salt product by forming a reactive admixture comprising (a) an unsaturated fatty acid glyceride feedstock; and (b) from about 1 mol to about 3 mol of at least one monovalent metal hydroxide or at least one divalent metal hydroxide; and heating the admixture to a temperature at which said fatty acid glycerides saponify to form fatty acid metals salts; wherein said monovalent metal is potassium; and wherein said divalent metal is selected from the group consisting of calcium, copper, magnesium and zinc. The fatty acid glycerides may be saponified in an atmosphere in which the partial pressure of oxygen has been reduced by an amount effective to provide an improvement in storage stability until a free-flowing, storage-stage product is obtained, or prior to saponification, the fatty acid glycerides may blended with a stabilizing oil that promotes storage stability, or both. Storage stable metal salts of unsaturated fatty acids prepared by the inventive methods are also disclosed.

88 Claims, 3 Drawing Sheets

U.S. PATENT DOCUMENTS

| | | | |
|---|---|---|---|
| 4,298,730 A | 11/1981 | Galleymore et al. |
| 4,472,432 A | 9/1984 | Iwamura et al. |
| 4,495,201 A | 1/1985 | Bondar et al. |
| 4,642,317 A | 2/1987 | Palmquist et al. |
| 4,826,694 A | 5/1989 | McAskie |
| 4,853,233 A | 8/1989 | McAskie |
| 4,909,138 A | 3/1990 | McAskie |
| 5,043,328 A | 8/1991 | Weithmann |
| 5,143,737 A | 9/1992 | Richardson |
| 5,234,701 A | 8/1993 | Cummings et al. |
| 5,382,678 A | 1/1995 | Vinci et al. |
| 5,430,066 A | 7/1995 | Cook et al. |
| 5,456,927 A | 10/1995 | Vinci et al. |
| 5,541,225 A | 7/1996 | Leaf et al. |
| 5,554,646 A | 9/1996 | Cook et al. |
| 5,604,258 A | 2/1997 | Ferrante et al. |
| 5,618,558 A | 4/1997 | Horrobin et al. |
| 5,681,971 A | 10/1997 | Scheibel et al. |
| 5,763,484 A | 6/1998 | Horrobin |
| 5,767,156 A | 6/1998 | Ferrante et al. |
| 5,804,210 A | 9/1998 | Cook et al. |
| 5,814,663 A | 9/1998 | Cook et al. |
| 5,837,731 A | 11/1998 | Vaddadi |
| 5,859,055 A | 1/1999 | Horrobin et al. |
| 5,861,433 A | 1/1999 | Akimoto et al. |
| 5,888,541 A | 3/1999 | Horrobin et al. |
| 5,914,346 A | 6/1999 | Cook et al. |
| 5,968,792 A | 10/1999 | Wenzel et al. |
| 6,020,378 A | 2/2000 | Cook et al. |
| 6,034,132 A | 3/2000 | Remmereit |
| 6,229,031 B1 | 5/2001 | Strohmaier et al. |
| 6,559,324 B2 | 5/2003 | Strohmaier et al. |
| 6,576,667 B2 * | 6/2003 | Strohmaier et al. | 514/560 |
| 6,737,078 B1 | 5/2004 | Kelley |
| 2003/0092923 A1 | 5/2003 | Strohmaier et al. |

FOREIGN PATENT DOCUMENTS

| | | |
|---|---|---|
| WO | WO 99/66877 A2 | 12/1999 |
| WO | WO02/26666 A | 4/2002 |
| WO | WO2004/098312 A | 11/2004 |

OTHER PUBLICATIONS

Formo et al., "Hydrolis," Bailey's Industrial Oil and Fat Products, 4.sup.th ed., vol. 1, pp. 100-103 (1979).

Formo et al., "Fat Splitting," Bailey's Industrial Oil and Fat Products, 4.sup.th ed., vol. 2, pp. 97-113 (1979).

* cited by examiner

POLYUNSATURATED FATTY ACID MONOVALENT AND DIVALENT METAL SALT SYNTHESIS

CROSS-REFERENCE TO RELATED APPLICATIONS

The present application is a National Stage of International Application No. PCT/US2005/014884, filed Apr. 29, 2005, which claims priority benefit under 35 U.S.C. §119(e) of U.S. Provisional Application No. 60/566,972 filed Apr. 30, 2004and is also a Continuation-In-Part of U.S. patent application Ser. No. 10/716,292 filed Nov. 18, 2003, which in turn is a Continuation-In-Part of U.S. patent application Ser. No. 10/299,337 filed Nov. 18, 2002, which in turn claims priority benefit under 35 U.S.C. §119(e) of U.S. Provisional Application No. 60/334,471 filed Nov. 16, 2001. The disclosures of all of which are incorporated herein by reference.

BACKGROUND

The present invention relates to the preparation of unsaturated fatty acid monovalent and divalent metal salt nutritional supplements from high glyceride content polyunsaturated oils, including marine oils. The present invention particularly relates to fatty acid monovalent and divalent metal salts rich in desirable unsaturated fatty acids such as omega-3, omega-6, and omega-9 fatty acids, including eicosapentaenoic acid (EPA), docosahexaenoic acid (DHA), decosopentaenoic acid (DPA), linoleic acid (LA), arachidonic acid (AA), and linolenic acid (ALA).

Certain divalent metals such as calcium, copper, magnesium and zinc have long been recognized as beneficial mineral nutrients for humans and certain companion animals and livestock, such as ruminants, horses, dogs, cats, rabbits, hamsters, birds, fish, and the like. For example, the mineral calcium not only builds and strengthens bones and teeth, it also maintains normal heartbeat and regulates blood pressure. It is also essential for the healthy functioning of the nervous system.

Copper is a key component of many enzyme systems. Copper deficiency is known to cause anemia, diarrhea, bone disorders, neonatal ataxia, changes in hair and wool pigmentation, infertility, cardiovascular disorders, impaired glucose and lipid metabolism and a depressed immune system.

As a positively charged divalent cation, magnesium acts as a calcium antagonist at the cell membrane level which is necessary to maintain normal electrical potentials and to coordinate muscle contraction-relaxation responses. Additionally, magnesium has roles in energy metabolism as a required cofactor for enzymes that catalyze fatty acid synthesis, protein synthesis, and glucose metabolism. Zinc also is essential for protein synthesis, integrity of cell membranes, maintenance of DNA and RNA, tissue growth and repair, wound healing, taste acuity, prostaglandin production, bone mineralization, proper thyroid function, blood clotting and cognitive functions.

A variety of unsaturated fatty acids have been identified as desirable for producing a diversity of nutritional and physiological benefits in humans and lower animals, including companion animals and livestock, and accordingly have attracted attention as nutritional supplements. In certain animals, omega-3 fatty acids for example, have been discovered to promote fertility, promote healthy skin and coat, reduce inflammation, and have other nutritional and physiological properties as well. In humans, it is believed that omega-3 fatty acids such as EPA and DHA support healthy cardiovascular function, are important for visual and neuronal development, support healthy blood levels of cholesterol, triglycerides and very low density lipoproteins, ease the inflammation associated with overuse of joints, and improve carbohydrate metabolism.

Conjugated Linoleic Acids (CLA's) have been discovered to possess a diverse and complex level of biological activity. Anticarcinogenic properties have been well documented, as well as stimulation of the immune system. U.S. Pat. No. 5,914,346 discloses the use of CLA's to enhance natural killer lymphocyte function. U.S. Pat. No. 5,430,066 describes the effect of CLA's in preventing weight loss and anorexia by immune system stimulation.

CLA's have also been found to exert a profound generalized effect on body composition, in particular, upon redirecting the partitioning of fat and lean tissue mass. U.S. Pat. Nos. 5,554,646 and 6,020,378 disclose the use of CLA's for reducing body fat and increasing lean body mass. U.S. Pat. No. 5,814,663 discloses the use of CLA's to maintain an existing level of body fat or body weight in humans. U.S. Pat. No. 6,034,132 discloses the use of CLA's to reduce body weight and treat obesity in humans. CLA's are also disclosed by U.S. Pat. No. 5,804,210 to maintain or enhance bone mineral content.

It is also known that supplementing the diet of livestock with unsaturated fatty acids will alter the livestock fatty acid profile, so that, for example, feeding dairy cows and beef cattle a source of unsaturated fatty acids beneficial to humans will yield dairy and beef products for human consumption enriched with the beneficial unsaturated fatty acids. For example, U.S. Pat. No. 5,143,737 discloses that the unsaturated fat content of milk and meat from ruminant animals can be increased by incorporating the intended unsaturated fat into the diet of the ruminant.

Thus, meat and milk enriched with CLA's and other unsaturated fatty acids can be obtained by supplementing ruminant diets with unsaturated fatty acids such as CLA. Dairy cows and beef cattle fed a source of CLA not only will produce lower fat content dairy and beef products, the products will be enriched with CLA's as well. Dietary supplementation of dairy cows and beef cattle with unsaturated fatty acids beneficial to humans can also be used to displace and thereby reduce the levels of undesirable saturated fatty acids in dairy and beef products.

The beneficial effects produced by unsaturated fatty acids are not limited to CLA's. Other unsaturated fatty acids are disclosed to be useful for treating diabetes (U.S. Pat. No. 4,472,432), heart disease (U.S. Pat. Nos. 4,495,201; 5,541,225 and 5,859,055), prostaglandin deficiencies (U.S. Pat. No. 5,043,328), malaria (U.S. Pat. No. 5,604,258), osteoporosis (U.S. Pat. Nos. 5,618,558 and 5,888,541), cancer (U.S. Pat. No. 5,763,484), immune system function (U.S. Pat. No. 5,767,156), Huntington's Chorea (U.S. Pat. No. 5,837,731) and inflammation (U.S. Pat. No. 5,861,433). The disclosures of the foregoing patents are all incorporated by reference.

It has further been discovered that ruminants fed a source of trans-C18:1 fatty acids will have decreased concentrations of milk fat, hepatic triacylglycerol, and lower incidence of sub-clinical ketosis during early postpartum, and that feeding a source of linoleic (C18:2) fatty acids during the transition period will increase synthesis of $PGF_{2V}$. The linoleic fatty acids thus hasten uterine involution and reduce the incidence of clinical and subclinical uterine inflammation; which translates to increased fertility.

Fatty acids are obtained through conversion of glycerides by either hydrolysis or saponification. Because of their fragile stability and complex degradation kinetics, certain unsaturated fatty acids, such as omega-3 fatty acids, have been difficult to incorporate into acceptable and effective nutritional supplements that are easily manufactured.

While monovalent and divalent salts of saturated and unsaturated fatty acids have shown exceptional storage stability, unsaturated fatty acids typically do not readily react to form calcium salts using the processes known in the art such as those disclosed in U.S. Pat. Nos. 5,143,737, 4,642,317; 4,826,694; 4,853,233 and 4,909,138. Instead of forming free-flowing granules, a mass develops that hardens into a tough material that resists grinding into the fine particles required for manufacturing nutritional supplements. The resulting material also lacks storage stability. The product tends to auto-oxidize through an exothermic reaction that leads to a congealing of the product mass from its free flowing granular state to a hard amorphous state.

U.S. Pat. No. 6,576,667 discloses methods by which calcium salts of unsaturated fatty acids having as high as 60 percent by weight glycerides can be prepared. The disclosure of this patent is incorporated by reference. However, commercial sources of unsaturated fatty acids such as marine oils have glyceride contents as high as 100 percent by weight, which remain difficult to convert to storage stable free-flowing fatty acid divalent metal salts. U.S. Pat. No. 6,576,667 addresses this problem by diluting the high glyceride content oils to glyceride levels below 60 weight percent with lower glyceride content fatty acid feedstocks such as Palm Fatty Acid Distillates (PFAD's). However, this also reduces the unsaturated fatty acid concentration in the fatty acid calcium salt product, requiring greater quantities to be fed as part of a feed ration to adequately supplement the ruminant diet.

U.S. Pat. No. 6,229,031 discloses a saponification method by which calcium salts of fatty acids having as high as 100 percent by weight glycerides can be prepared. The disclosure of this patent is also incorporated by reference. However, calcium salts prepared from fatty acids with a significant degree of unsaturation prepared by this method have been discovered to lack storage stability.

A need exists for a method by which monovalent and divalent metal salts of unsaturated fatty acids having acceptable storage stability can be prepared.

SUMMARY OF THE INVENTION

This need is met by the present invention. It has now been discovered that improvements in the storage stability of saponified unsaturated fatty acid monovalent and divalent metal salts can be significantly improved by performing the saponification method of U.S. Pat. No. 6,229,031 in an atmosphere in which the partial pressure of oxygen has been reduced. While it is known to exclude oxygen from a reaction process to prevent explosion or fire, or the oxidation of the ingredients and end product at elevated temperatures during the course of a reaction, what was unexpected is that minimizing atmospheric oxygen in the method of the present invention also improves the shelf life and storage stability of the finished product long after the reaction is completed.

It has further been discovered that the shelf life and storage stability of saponified unsaturated fatty acid monovalent and divalent metal salts can also be improved by blending an effective amount of a stabilizing oil with the reactive admixture prior to saponification in order to provide an antioxidant effect. The method that includes blending the stabilizing oil with the admixture may be carried out in an atmosphere in which the partial pressure of oxygen has or has not been reduced.

The shelf life and storage stability of unsaturated fatty acid monovalent and divalent metal salt products varies with unsaturated fatty acid content and degree of unsaturation. Shelf life decreases as the degree of polyunsaturation increases, with susceptibility to oxidation increasing 10-fold with every additional double bond in a fatty acid.

Unsaturated fatty acid divalent metal salt products must possess sufficient shelf life and storage stability to pass without objection in the field. For purposes of the present invention, "shelf life" is defined as the time period required before product degradation exceeds levels considered acceptable to those of ordinary skill in the art. For a product to have adequate storage stability, the shelf life must exceed the amount of time the product would be expected to spend in storage after manufacture and before being consumed. Typically this is about six months.

Minor quantities of polyunsaturated fatty acids with greater than 3 double bonds will reduce product shelf life to unacceptable levels. At lower mono-unsaturated fatty acid concentrations the presence of polyunsaturated fatty acids will result in storage instability in an otherwise stable mono-unsaturated fatty acid monovalent or divalent metal salt product with an adequate shelf life. Nevertheless, many fatty acid glyceride sources have mono- and polyunsaturated fatty acid levels that will produce a storage stable monovalent or divalent metal salt product. Palm oil calcium salts, for example, possess adequate storage stability when prepared by the method of U.S. Pat. No. 6,229,031.

The methods of the present invention are thus particularly useful when used to saponify fatty acid glycerides with levels of mono- and polyunsaturated fatty acids that would otherwise produce an unstable monovalent or divalent metal salt product when saponified in the presence of oxygen or in the absence of an antioxidant-effective amount of a stabilizing oil. For purposes of the present invention, such fatty acid glycerides are fatty acid feedstocks with an unsaturated fatty acid concentration sufficient to form unstable monovalent and divalent metal salt products when saponified in an ambient atmosphere or in the absence of an antioxidant-effective amount of a stabilizing oil, wherein unstable monovalent or divalent metal salt products are defined as monovalent or divalent metal salt products with an inadequate "shelf life" as that term is defined in the present specification.

Therefore, one aspect of the present invention is a method for the preparation of a free-flowing, storage-stable fatty acid metal salt product by forming a reactive admixture of (a) an unsaturated fatty acid glyceride feedstock and (b) from about 1 mol to about 3 mol of at least one monovalent metal hydroxide or at least one divalent metal hydroxide, and then heating the admixture to a temperature at which the fatty acid glycerides saponify to form fatty acid monovalent or divalent metal salts in an atmosphere in which the partial pressure of oxygen has been reduced by an amount effective to provide an improvement in storage stability, until a free-flowing, storage-stable product is obtained; wherein the monovalent metal is potassium and the divalent metal is selected from calcium, copper, magnesium and zinc.

The partial pressure of oxygen in the reactive atmosphere may be reduced by inert gas blanketing of the admixture with, for example, nitrogen, carbon dioxide or argon, or by heating the admixture under vacuum. Nitrogen blanketing methods are preferred, as are methods in which atmospheric oxygen is essentially eliminated.

Another aspect of the present invention provides a method for the preparation of a free-flowing, storage-stable fatty acid metal salt product comprising: forming a reactive admixture comprising (a) an unsaturated fatty acid glyceride feedstock;

(b) an antioxidant-effective amount of a stabilizing oil to provide an improvement in storage stability; and (c) from about 1 mol to about 3 mol of at least one monovalent metal hydroxide or at least one divalent metal hydroxide; and heating the admixture to a temperature at which said fatty acid glycerides saponify to form fatty acid metal salts until a free-flowing, storage-stable product is obtained; wherein the fatty acid profile of said stabilizing oil is more resistant to oxidation than the fatty acid profile of said glyceride feedstock; and wherein said monovalent metal is potassium; and said divalent metal is selected from the group consisting of calcium, magnesium, copper and zinc.

Additional embodiments of this aspect of the invention include methods in which the partial pressure of oxygen is reduced in the reactive atmosphere to provide further improvements in storage stability. The partial pressure of oxygen in the reactive atmosphere may be reduced by inert gas blanketing of the admixture or by heating the admixture under vacuum as described above.

The saponification methods of the present invention are typically applied to fatty acid glyceride feedstocks having greater than about 45% by weight of the fatty acid content in the form of fatty acid glycerides, and having an unsaturated fatty acid concentration sufficient to form unstable monovalent or divalent metal salt products when saponified in an ambient atmosphere or in the absence of a stabilizing oil. Such fatty acid glyceride feedstocks may be comprised of a mixture of two or more $C_{10}$-$C_{22}$ fatty acids. The methods can be used to prepare storage-stable products from unsaturated fatty acid sources, such as marine oils, having glyceride levels as high as 100% by weight.

According to another aspect of the present invention storage-stable unsaturated fatty acid metal salt products are provided that are prepared by the methods of the present invention. Such products can assume the form of powders, granules, paste, pellets, emulsion, colloidal suspension, non-colloidal suspension, capsules, and tablets, and may be administered orally, rectally, or topically. Moreover, such products may also comprise vitamins, antioxidants, amino acids, sugars and complex carbohydrates, trace nutritional elements, medicaments, proteins, anabolic steroids, hormones related to pregnancy or lactation, herbal supplements, *lactobacillus* micro-organisms, and cosmetological active ingredients.

The present invention thus provides storage-stable metal salts of unsaturated fatty acids beneficial to humans, companion animals, and livestock from feedstocks for those acids that are typically very high in glyceride content, without having to significantly dilute the feedstock, if at all, with low glyceride content feedstocks that contain little, if any, of the beneficial unsaturated fatty acids. Thus, essentially any unsaturated oil containing useful levels of beneficial unsaturated fatty acids is suitable for use with the present invention, and for purposes of the present invention is included within the definition of an unsaturated oil.

The present invention can be used with unsaturated oils having what was until now considered a low level of beneficial unsaturated fatty acids among the total unsaturated fat content, because with the present invention there is no need to dilute the feedstock with saturated fatty acids and the unsaturated fatty acid concentration is essentially conserved over time. Storage-stable metal salts of unsaturated oils containing between about 3 and about 100 weight percent unsaturated fatty acids based on the total fatty acid content can be formed using the methods of the present invention. Oils with lower levels of beneficial unsaturated fatty acids may be used if they have utility based on their beneficial unsaturated fatty acid content.

Among the beneficial unsaturated fatty acids, beneficial polyunsaturated fatty acids are particularly preferred, and especially omega-3 fatty acids such as EPA, DHA, DPA and ALA, and omega-6 fatty acids such as linoleic acid, CLA's and arachidonic acid, because of their reproductive and other benefits. Oils which are a high glyceride content source of omega-3 and omega-6 fatty acids, such as marine oils, may be directly saponified by the method of the present invention to form storage-stable metal salt products without first diluting the oil with saturated fatty acids. The resulting products contain storage-stable levels of polyunsaturated fatty acids as omega-3 and omega-6 fatty acid metal salts that heretofore could not be attained using prior art methods.

Therefore, according to yet another aspect of the present invention a free-flowing storage-stable fatty acid metal salt product is provided containing at least one unsaturated fatty acid, wherein the total unsaturated fatty acid content is between about 40 and about 95% by weight. Preferred products contain beneficial polyunsaturated fatty acids such as omega-3 and omega-6 fatty acids, with a product containing at least one polyunsaturated fatty acid selected from DHA, EPA, DPA, ALA, linoleic and arachidonic acid, each at a level between about 1 and up to about 80% by weight being particularly preferred. Conjugated polyunsaturated fatty acids such as CLA's are also preferred.

The DHA- and EPA-containing fatty acid metal salts enhance the fertility of ruminants and other animals, including humans. Therefore, according to still yet another aspect of the present invention, a method is provided for increasing fertility in a animal, in which the animal is fed an effective amount of the EPA- and DHA-containing fatty acid metal salts of the present invention.

The method according to this aspect of the present invention is particularly effective to enhance the fertility of ruminants, especially dairy cows. Methods in accordance with this aspect of the present invention begin feeding the supplements daily to a female ruminant from about 21 days before to about 28 days after parturition. The present invention includes methods in which the feeding continues at least until conception occurs.

The fertility enhancement obtained by the metal salts of the present invention also includes a reduction in embryonic death in the months following conception. Therefore, methods in accordance with the present invention continue feeding the supplements for at least 30 days, and preferably for at least 60 days after conception.

According to an additional embodiment, a nutritional supplement comprising an effective amount of a fatty acid metal salt of the present invention is also provided. Also disclosed is a method of supplementing the diet of an animal comprising administering to the animal an effective amount of a fatty acid metal salt of the present invention. A method is also provided in which an effective amount of at least one nutritionally beneficial fatty acid metal ("NBFAM") salt is applied to a pet food formulation. For purposes of the present invention "applied" is defined as including both adding an effective amount of at least one NBFAM salt to a moist pet food formulation or a dry or semi-dry pet food formulation prior to extrusion, as well as coating an extruded dry or semi-dry pet food composition with an effective quantity of at least one NBFAM salt after the pet food composition has been extruded.

The NBFAM salt can be applied to kibbles as a dry powder via a dusting process, or may be sprayed onto the kibbles as a liquid suspension. The NBFAM salt is preferably applied in an amount sufficient to contribute from about 0.01 to about 5.0% by weight of one or more NBFAM salts by weight to the pet food composition.

The present invention also includes moist pet food compositions and extruded dry and semi-dry pet food compositions to which the NBFAM salts of the present invention have been added.

The foregoing and other objects, features and advantages of the present invention are more readily apparent from the detailed description of the preferred embodiments set forth below, taken in conjunction with the accompanying drawings.

DETAILED DESCRIPTION OF PREFERRED EMBODIMENTS

Figure 1:
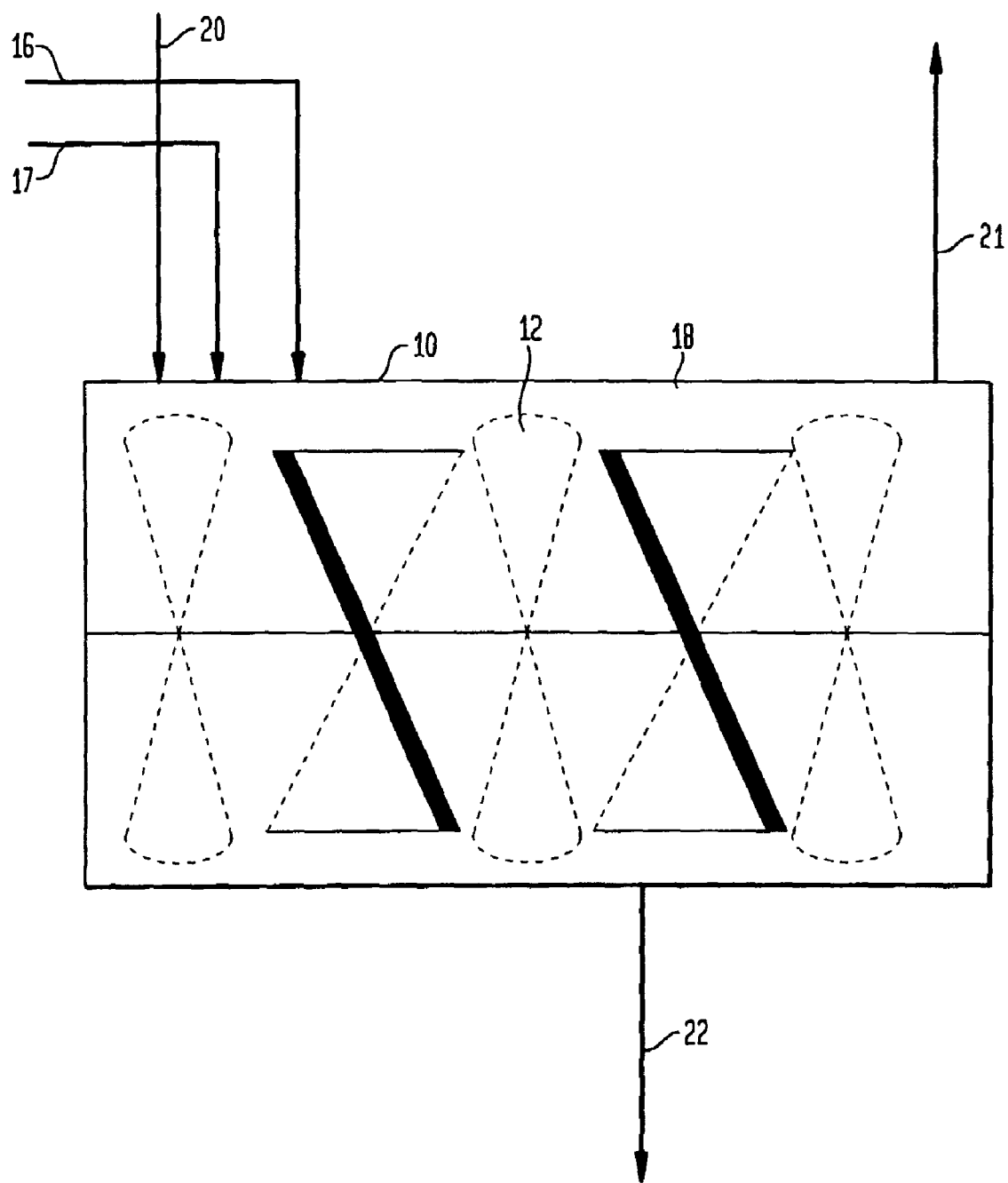
FIG. 1 depicts a batch process according to one embodiment of the present invention.

The present invention provides processes by which unsaturated marine, animal, and vegetable fats, oils and other unsaturated fatty acid glyceride content materials may be converted to storage-stable fatty acid monovalent and divalent metal salts having utility as nutritional supplements for humans and animals. Monovalent metal salt means a salt of any biocompatible metal having a valence of one, such as potassium. Divalent metal salt means a salt of any biocompatible metal having a valence of two, such as calcium, copper, magnesium, and zinc. The divalent metals copper and zinc provide particularly unique nutritional benefits. By biocompatible it is meant having the property of being biologically compatible by not producing a toxic, injurious, or immunological response in living tissue. These salts may be in the form of free-flowing powders, granules, paste, or pellets, or may be in the form of an emulsion, colloidal suspension, non-colloidal suspension, capsules, or tablets.

Typical fatty acid feedstocks range in fatty acid content between $C_{10}$ and $C_{22}$ fatty acids and fatty acid glycerides. The term "glyceride" as employed herein includes $C_{10}$-$C_{22}$ fatty acid monoglycerides, diglycerides and triglycerides, and any mixture thereof. The economic advantages provided by the present invention are obtained when using fatty acid feedstocks having glyceride concentrations that prevent the formation of stable monovalent and divalent metal salt products or when using fatty acid feedstocks with unsaturated fatty acid concentrations that prevent the formation of stable monovalent and divalent metal salts through high temperature saponification in an ambient atmosphere or in the absence of a stabilizing oil having antioxidant effects. Usually, fatty acid feedstocks cannot be hydrolyzed and neutralized to form stable monovalent and divalent metal salts at glyceride contents of about 45% by weight and greater. However, the methods of the present invention can be employed with fatty acid feedstocks in which from about 15% to about 100% by weight of the fatty acids are in glyceride form. The methods of the present invention will also form monovalent and divalent metal salts using lower glyceride content fatty acid feedstocks, and with glyceride-free fatty acid feedstocks.

The methods of the present invention will improve the storage stability of essentially any saponified unsaturated fatty acid monovalent or divalent metal salt product, even those considered by the ordinarily skilled artisan to be adequately storage stable. When the level of polyunsaturated fatty acids is less than about 20% by weight, significant improvement in monovalent and divalent metal salt product stability is obtained for fatty acid feedstocks with total unsaturated fatty acid concentrations greater than about 50% by weight. When the level of polyunsaturated fatty acids is between about 20 and about 90% by weight, significant improvement in monovalent and divalent salt product stability is obtained for fatty acid feedstocks with total unsaturated fatty acid concentrations greater than about 25% by weight.

Thus, the processes of the present invention can be used to prepare fatty acid monovalent and divalent metal salts from pure unsaturated oils of marine, animal, or vegetable origin, including those disclosed in the above-referenced U.S. Pat. No. 6,576,667. Examples of suitable vegetable oils include soybean oil, cottonseed oil, linseed oil, canola oil, and the like, and oils derived from marine vegetation such as algae, kelp, and the like. Examples of marine oil sources include menhaden, herring, mackerel, caplin, tilapia, tuna, sardine, pacific saury, krill, salmon, anchovy, skates, whale, seal, crab, shrimp, lobster, eel, mollusk, and the like.

Such fatty acid glyceride feedstocks typically contain from about 10 to about 100 weight % of the fatty acid content in the form of fatty acid glycerides, from about 0 to about 90% by weight of free fatty acids, and less than 5% by weight of moisture, insolubles and unsaponifiables. The feedstocks also typically contain from about 10 to about 95% by weight, and preferably between about 20 and about 90% by weight, of total unsaturated fatty acids, with between about 15 and about 80% by weight of the total unsaturated fatty acid content being polyunsaturated. The methods of the present invention thus provide storage stable fatty acid monovalent and divalent metal salts containing between about 15 and about 85% by weight of one or more unsaturated fatty acids based on total product weight, of which between about 10 and about 80% by weight are one or more polyunsaturated fatty acids. The monovalent and divalent metal salts contain less than 10% by weight, and preferably less than 1% by weight of unreacted glycerides.

Other conventional biologically active materials can be added to the monovalent and divalent metal salt products at conventional levels by known means. By the term "biologically active material", it is meant any substance capable of being administered to a living organism that produces a physiological or biochemical effect on one or more vital processes occurring in that living organism. The biologically active material can be selected from a broad variety of nutrients and medicaments, either as a single component or as a mixture of components, which are illustrated by the following list of active molecular species:

1. Sugars and complex carbohydrates which include both water-soluble and water-insoluble monosaccharides, disaccharides, and polysaccharides. Particularly preferred carbohydrates include cane molasses and sugar beet byproducts.

2. Amino acid ingredients, either singly or in combination, which include arginine, histidine, isoleucine, leucine, lysine, methionine, phenylalanine, threonine, tryptophan, valine, tyrosine ethyl HCl, alanine, aspartic acid, glutamic acid, sodium glutamate, potassium glutamate, glycine, proline, serine, cystine ethyl HCl, and the like; and analogues and salts thereof.

3. Vitamin ingredients, either singly or in combination, including thiamine HCl, riboflavin, pyridoxine HCl, niacin, inositol, choline chloride, calcium pantothenate, biotin, folic acid, ascorbic acid, p-aminobenzoic acid, cobalamin, n-dimethylglycine, calcium pangamate, choline bitartrate, thiamin, niacin, pantethine, beta-carotene, lutein, lycopene, chondroitin, glucosamine, d-alpha tocopherol, calciferol, and derivatives of 2-methyl-1,4-naphthoquinone, and the like.

4. Trace element ingredients, either singly or in combination, including compounds of cobalt, tin, nickel, chromium, molybdenum, iodine, chlorine, silicon, vanadium, iodine, sodium and potassium.

5. Protein ingredients as obtained from sources such as cottonseed meal, soybean meal, canola meal, sunflower seed meal, safflower meal, dehydrated alfalfa, corn gluten meal, soybean protein concentrate and potato protein, marine meal, marine and poultry protein isolates, crab protein concentrate, hydrolyzed protein feather meal, poultry byproduct meal, liquid or powdered egg, milk whey, egg albumen, casein, marine solubles, cell cream, brewer's residues, and the like.

6. Medicament ingredients, either singly or in combination, including promazine hydrochloride, chloromedoniate acetate, chlorotetracycline, sulfamethazine, monensin, sodium monensin, poloxaline, oxytetracycline, BOVATEC, streptomycin, and the like.

7. Antioxidants, including butylated hydroxyanisole, butylated hydroxytoluene, tertiary-butylhydroquinone, tocopherols, propyl gallate and ethoxyquin; and preservatives, including sodium sorbate, potassium sorbate, sodium benzoate, propionic acid, α-hydroxybuteric acid, and the like.

8. Herbal supplements, including St. John's Wart, echinacea, Goldenseal, and ginkgo, aloe, astragalus, black cohosh root, sarsaparilla root, Siberian ginseng root, licorice root, blessed thistle herb, squaw vine herb and false unicorn root. bladderwrack, cascara sagrada, chamomile, chickweed, damiana leaves, devil's claw, dong quai, hoelen, ophiopogon, scute, platycodon, citrus morus root, fritillary, gardenia, shizandra, *Camellia sinensis* (green tea), and *Lavandula officinalis, Carthamus tinctorius, Simmondsia chinensis, Sesamum indicum, Vitis vinifera, Persea gratissima, cucumis sativus*, organic *Macrocystis pynfera*, and the like.

9. *Lactobacillus* micro-organisms, including *Acidophilus, Bifidus*, and *Rhamnosus*, and the like.

10. Cosmetological active ingredients, including bisabolol, phytantriol, retinol, benzophenone-1, and the like.

11. Hormones involved in pregnancy and lactation, including chorionic gonadotrophin, progesterone, estrogen, fetal adrenal axis hormones, relaxin, prostaglandins, prolactin, oxytocin, and the like.

12. Anabolic steroids including tetrahydrogestrinone, trenbolone, gestrinone, and the like.

While the calcium salts of the present invention can be used as rumen-inert feed supplements for ruminants such as cattle, these and other unsaturated fatty acid divalent metal salts are also useful in general as a nutritional supplement for humans and other mammals, including pets such as dogs and cats, and non-mammals, including birds and fishes, when formulated to contain unsaturated fatty acids beneficial to the respective species. The beneficial unsaturated fatty acid calcium salt nutritional supplements can also be fed to livestock to produce meat, poultry and dairy products enriched with the beneficial unsaturated fatty acids for consumption by species for which the unsaturated fatty acids are beneficial.

Examples of specific unsaturated fatty acids that are beneficial to humans, livestock, pets, birds or fishes, and which can be converted by the saponification method of the present invention to storage-stable fatty acid monovalent and divalent metal salts, include linoleic acid (C18:2), arachidonic acid (C20:4) and isomers thereof, omega-3 fatty acids such as DHA, EPA, DPA, ALA, and the like, omega-6 fatty acids, CLA isomers having utility as human dietary supplements, including the 10,12 and 9,11 isomers, specific examples of which include the trans 10, trans 12; trans 10, cis 12; cis 10, trans 12; cis 10, cis 12; trans 9, trans 11; trans 9, cis 11; cis 9, trans 11 and cis 9, cis 11 isomers, trans fatty acids isomers having utility as dietary supplements for livestock, including C18:1 isomers such as trans-9-octadecenoic acid. A particularly preferred product contains at least one polyunsaturated fatty acid selected from, about 1 to about 25% by weight DHA, about 1 to about 25% by weight EPA, about 1 to about 25% by weight DPA, about 1 to about 75% by weight ALA, about 0.5 to about 10% by weight arachidonic acid, about 1 to about 80% by weight linoleic acid and about 1 to about 80% by weight CLA.

The fatty acid monovalent and divalent metal salts are prepared by adding a monovalent metal hydroxide, such as KOH, or a divalent metal hydroxide, such as $Ca(OH)_2$, $Cu(OH)_2, Mg(OH)_2$, and $Zn(OH)_2$, to the fatty acid glyceride-containing feedstock in the range of from about 1 mol to about 3 mol. A monovalent or divalent metal hydroxide level from about 1 mol to about 2 mol is preferred.

Additional heat is added to the admixture, if necessary, to increase the temperature to a range between about 150 and about 300° C., and preferably between about 200 and about 270° C. In accordance with the present invention, the monovalent metal hydroxide may be substituted by a stoichiometric equivalent of a monovalent metal oxide (such as $K_2O$) or the divalent metal hydroxide may be substituted by a stoichiometric equivalent of divalent metal oxide (such as CaO, CuO, MgO, and ZnO) and water, and for purposes of the present invention the terms "monovalent metal hydroxide" and "divalent metal hydroxide" in the claims are defined as including the replacement in the reactive admixture of the monovalent metal hydroxide or the divalent metal hydroxide by a stoichiometric quantity of a monovalent metal oxide, or a divalent metal oxide, respectively, and water.

Any of the processes of the present invention can be performed under vacuum, ambient pressure, or at an elevated pressure to maintain the desired temperature. Further, the reactions may be performed in an atmospheric environment in which the partial pressure of oxygen is reduced to levels at which a storage-stable saponified monovalent or divalent metal salt product will form. Oxygen level reduction may be achieved either by purging a sealed reaction vessel with an inert gas such as nitrogen, carbon dioxide or argon, or by drawing a vacuum. Methods for inert gas purging and vacuum drawing are essentially conventional and well known to those skilled in the art. For example, inert gas purging can be accomplished using an inert gas blanket consisting of, for example, nitrogen, carbon dioxide or argon, at a flow rate between about 0.25 to about 50 liters per minute, and preferably between about 1.0 to about 20.0 liters per minute that is applied to the reaction vessel. A vacuum of between about 250 to about 750 mm Hg, and preferably between about 300 to about 500 mm Hg, should be drawn on the sealed vessel, and preferably using an inert gas such as nitrogen, carbon dioxide or argon as the vacuum gas.

Any reduction of the partial pressure of oxygen in the reactive atmosphere will provide an improvement in storage stability. The reduction needed to create a storage-stable product with an adequate shelf life will depend upon the level and degree of unsaturation in the fatty acid glycerides to be saponified, with higher levels and degrees of unsaturation requiring greater reduction in the oxygen content of the reactive atmosphere. Typically, if the partial pressure of oxygen is reduced, the partial pressure of oxygen should be less than about 100 torr, with partial pressures less than 50 torr preferred and partial pressures less that 10 torr even more preferred. The reduction in the partial pressure of oxygen is attained either by displacement of oxygen with the inert gas purge or by drawing a vacuum sufficient to attain a sufficient reduction in total pressure to reduce the partial pressure of oxygen to desired levels, or both.

The amount of time required for the saponification reaction is typically between about 1 to about 15 minutes, and more typically between about 2 and about 5 minutes. The stability of the monovalent metal salts or the divalent metal salts is improved by limiting the reaction time. The reaction is easily identified by the transformation of the admixture into a caramel-like mass. Upon further heating and agitating, the mass further transforms into a taffy-like material, which, upon transfer from the reaction vessel, can easily be processed into free-flowing particles.

In an alternate embodiment, the monovalent or divalent metal salt stability is improved by method steps that accelerate the reaction process and thereby limit the total quantity of heat to which the reactive admixture is exposed. According to this particular embodiment, the fatty acid feedstock is preheated to a temperature between about 177 and 288° C. and then rapidly combined with the monovalent or divalent metal salt at a rate effective to form a uniform, homogeneous mass having improved storage stability over products formed without preheating and rapid blending, typically within a minute. Preferred mixing rates will form a uniform homogeneous mass within one to 15 seconds. Adequate heat is supplied to the feedstock until a free-flowing storage-stable product is obtained.

In yet another embodiment, the monovalent or divalent metal salt stability is improved by blending an effective amount of a stabilizing oil having antioxidant effects with an unsaturated fatty acid glyceride feedstock and a monovalent or a divalent metal hydroxide prior to saponification. The stabilizing oil has a fatty acid profile that is more resistant to oxidation than the fatty acid profile of said glyceride feedstock. Typically, this occurs with a stabilizing oil having a fatty acid profile more saturated then the fatty acid profile of the glyceride feedstock. However, this is not universally true. For example, safflower and sunflower oils have been found to have a stabilizing effect upon marine oils despite having a less saturated fatty acid profile. One of ordinary skill in the art can identify stabilizing oils having fatty acid profiles more resistant to oxidation than the fatty acid profile of a given glyceride feedstock without undue experimentation.

In most situations, an oil that contains less fatty acids with 3 or more double bonds than a glyceride feedstock will be a stabilizing oil relative to that feedstock. Stabilizing oils typically comprise any oil or fat with an antioxidant-effective amount of fatty acids with 18 or less carbon atoms and 3 or less double bonds, such as, tallow, soy oil, linseed oil, stearin, or a combination thereof. Additionally, the stabilizing oil is present in an amount from about 10 to about 90 percent by weight, preferably between about 25 and about 50 percent by weight. As the amount of the stabilizing oil approaches the preferred range, the improved stability of the metal salt product increases. Without wishing to be bound by any particular theory, it is speculated that the stabilizing oil metal salt may form a protective matrix or protective dispersion with the less saturated fatty acid metal salt product.

The methods according to this embodiment may be performed, optionally, in a reactive atmosphere in which the partial pressure of oxygen is reduced in order to provide further improvements in storage stability. The partial pressure of oxygen in the reactive atmosphere may be reduced by inert gas blanketing of the admixture with, for example, nitrogen, carbon dioxide or argon, or by heating the admixture under vacuum. Nitrogen blanketing methods are preferred, as are methods in which atmospheric oxygen is essentially eliminated.

The processes of the present invention may be employed as either a batch or a continuous process. Examples of reaction vessels suitable for use with the present invention include continuous or batch reactors, indirectly or directly heated, with multiple agitation and shear elements, suitable for very high viscosity materials.

A batch process according to the present invention is depicted in FIG. 1. Fatty acid glycerides and a divalent metal hydroxide are added via lines 16 and 17, respectively, to the interior 18 of sealed production vessel 10 adapted to supply heat to the vessel contents (not shown), as well as to remove heat therefrom (not shown). The production vessel is equipped with blades 12 for mixing the vessel contents under adequate shear to form a homogenous admixture of the vessel contents.

The production vessel should also be adapted to remove oxygen from the reaction environment, either by forming a vacuum above the vessel contents, or by blanketing the vessel contents with an inert gas such as nitrogen, carbon dioxide or argon. Means by which this can be accomplished are well known to the artisan of ordinary skill. In the embodiment of FIG. 1, line 20 supplies a purge of inert gas to the sealed vessel, in this case nitrogen, which is vented via line 21. Line 21 can be readily adapted to draw a vacuum as well.

The reaction mixture is heated, reacted and cooled under either the inert gas purge and/or vacuum. After cooling, the mixer blades 12 grind the product into flakes and granules that are discharged from the rector at port 22.

Figure 2:
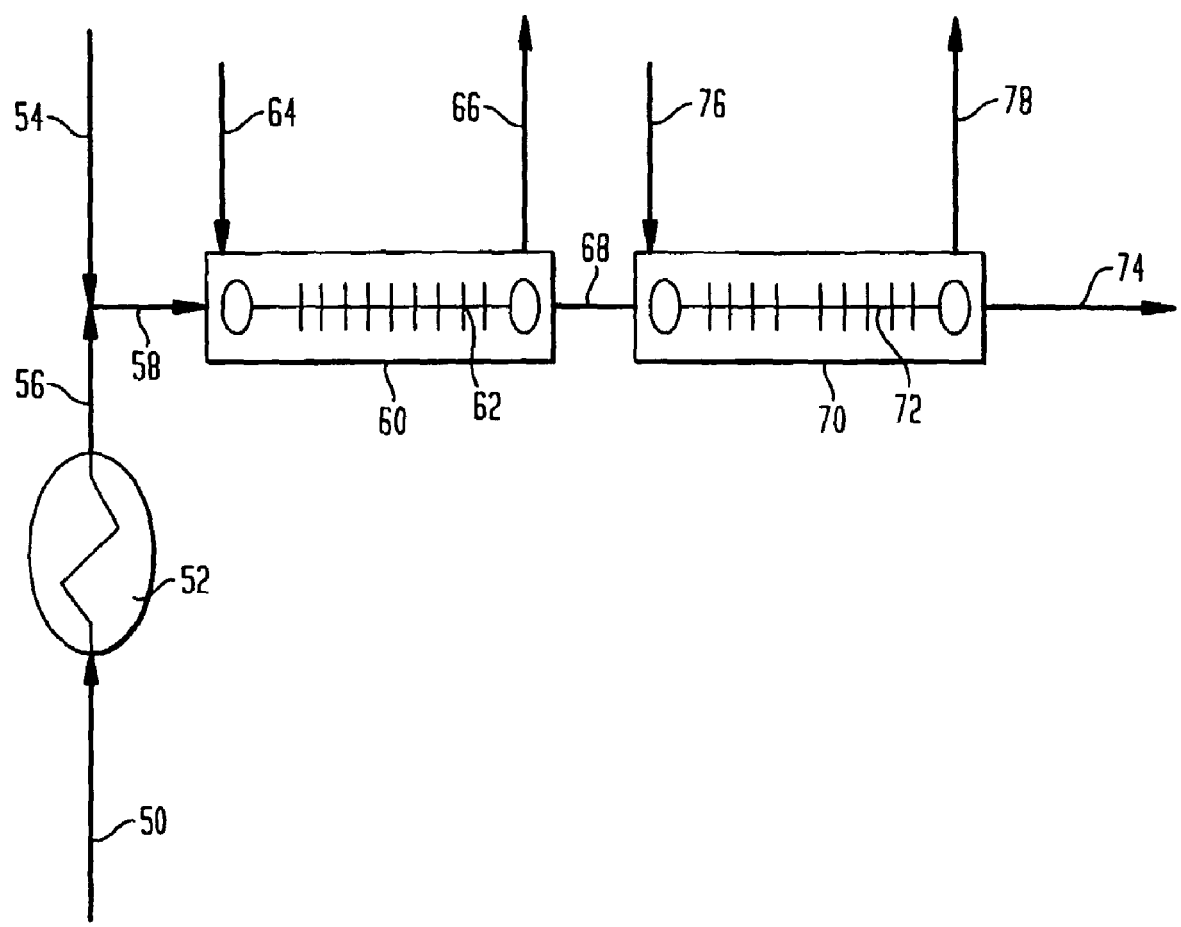
FIG. 2 depicts a continuous process according to another embodiment of the present invention.

A continuous process according to the present invention is shown in FIG. 2. Feedstock oils are supplied via line 50 to heater 52. Divalent metal hydroxide is supplied via line 54 and combined with the heated feedstock oil, which is supplied from the heater via line 56. The combination of divalent metal hydroxide and feedstock oil is then supplied via line 58 to reaction screw conveyor 60, the screw flight 62 of which functions to mix the contents under adequate shear to form a homogenous admixture thereof. The screw conveyor is adapted to supply heat to the reaction mixture (not shown).

Line 64 supplies a purge of inert gas, which in this case is also nitrogen, that exits via vent 66. These lines can also be adapted to draw a vacuum. The product is discharged via line 68 to cooling and grinding screw conveyor 70, the screw flight 72 of which functions to grind the product into flakes and granules that are discharged from screw conveyor 70 at port 74. Screw conveyor 70 is adapted to withdraw heat from the reacted mixture (not shown). Line 76 supplies a purge of inert gas, which is also nitrogen, that exits via vent 78. These lines can also be adapted to draw a vacuum.

The free-flowing particles produced by the aforementioned processes can subsequently be formulated into products of various forms including powders, granules, pastes, pellets, emulsions, colloidal suspensions, non-colloidal suspensions, elixirs, capsules, or tablets to be administered through a variety of techniques known in the art including, but not limited to, orally, rectally, or topically. Depending on the dosage form, it may be necessary to grind or mill the particles to obtain a particle size suitable for the manufacture thereof. Particle size requirements are well known to those skilled in the art of manufacturing products of this type.

Product compositions according to this invention may be prepared according to the customary methods, using one or more acceptable adjuvants or excipients. The adjuvants comprise, inter alia, diluents, sterile aqueous media, and various non-toxic organic solvents. The compositions may comprise sweeteners such as sucrose, lactose, fructose, saccharin, or Nutrasweet; flavorings such as peppermint oil, oil of wintergreen, cherry or orange flavorings, colorings, stabilizers such as methyl- or propyl-paraben in order to obtain biologically acceptable preparations.

The choice of vehicle and the content of the active substance in the vehicle are generally determined in accordance with the solubility and chemical properties of that product, the particular mode of administration, and the provisions to be observed in preparing the form of administration. For example, excipients such as lactose, sodium citrate, calcium carbonate, dicalcium phosphate, and disintegrating agents such as starch, alginic acids, and certain complex silica gels combined with lubricants such as magnesium stearate, sodium lauryl sulfate, and talc may be used for preparing tablets, troches, pills, capsules, and the like. To prepare a capsule, it is advantageous to use lactose and liquid carriers, such as high molecular weight polyethylene glycols. Various other materials may be present as coatings or to otherwise modify the physical form of the dosage unit. For instance, tablets, pills, or capsules may be coated with shellac, sugar, or both. When suspensions are used they may contain an emulsifying agent or agents, which facilitate suspension. Diluents such as sucrose, ethanol, polyols, such as polyethylene glycol, propylene glycol, and glycerol, or mixtures thereof may also be used. In addition, the divalent metal salt may be incorporated into sustained-released preparations and formulations.

For oral administration, the divalent metal salt may be administered, for example, with an inert or diluent or with an assimilable edible carrier, or it may be enclosed in hard or soft shell gelatin capsules, or it may be compressed into tablets, or it may be incorporated directly with the food of the diet, or may be incorporated with excipient and used in the form of ingestible tablets, buccal tablets, capsules, elixirs, suspensions, syrups, wafers, and the like.

For topical administration, gels (water or alcohol based), creams, or ointments containing compounds of the invention may be used. Such formulations are essentially conventional and include cosmetic formulations for the skin, hair, nails, and the like.

The fatty acid monovalent or divalent metal salts of the present invention function as rumen bypass feed supplements and may be conveniently fed to a ruminant admixed with a conventional ruminant feed. The feeds are typically vegetable materials edible by ruminants, such as legume hay, grass hay, corn silage, grass silage, legume silage, corn grain, oats, barley, distiller's grain, brewer's grain, soy bean meal and cottonseed meal and are included in an amount as typically recommended by a husbandry nutritionist, which ordinarily does not exceed 5% by weight of the dry solids content of the feed.

The monovalent and divalent metal salts are also useful in general as nutritionally beneficial fatty acid metal salt ("NBFAM") supplements for humans, other mammals, and non-mammals, including birds and fish. The percentage of NBFAM salt in the compositions of the invention may be varied. Additionally, several unit dosage forms may be administered at about the same time.

A dietician can readily determine suitable dosage amounts depending upon the needs of a human subject, for example, the desired therapeutic effect, the route of administration, the duration of the treatment, and the condition of the patient. In each particular case, the doses are determined in accordance with the factors distinctive to the patient to be treated, such as age, weight, general state of health, and other characteristics which can influence the efficacy of the compound according to the invention. For example, in an adult human, the daily dosages for oral administration are generally from about 0.01 to about 100 mg/kg body weight, preferably from about 0.1 to about 70 mg/kg body weight, more preferably from about 0.5 to about 10 mg/kg body weight per day.

Similarly, a person with animal husbandry knowledge can determine the appropriate dosage amounts for an animal subject, depending upon the needs and characteristics of the particular animal, such as, for example, route of administration, duration of the treatment, the general state of the animal's health, or any other category discussed above and considered applicable by one of skill in the field of animal husbandry.

Alternatively, methods in accordance with the present invention add an effective amount of the NBFAM salts of the present invention to a food product including pet food products such as cat food and dog food. Effective amounts include amounts that will provide a food product having a beneficial unsaturated fatty acid content between about 0.05 and about 1.5 weight percent. A beneficial unsaturated fatty acid content between about 0.1 weight percent and about 0.5 weight percent is preferred. Among the beneficial unsaturated fatty acids, polyunsaturated fatty acids, including conjugated polyunsaturated fatty acids, are preferred. This would include non-conjugated omega-3 and omega-6 fatty acids and conjugated fatty acids such as CLA's. Among the omega-3 fatty acids DHA, EPA, DPA and ALA are preferred. Among the omega-6 fatty acids, linoleic acids and arachidonic acids are preferred.

The present invention also includes food products containing the NBFAM salts of the present invention within the ranges described, including nutritionally supplemented human food products. Also disclosed are pet food products, such as cat food and dog food. The cat foods and dog foods include dry, semi-moist and moist cat food and dog food prepared by otherwise conventional methods from conventional formulations incorporating conventional pet food ingredients to which the NBFAM salts are added by techniques conventionally employed for the nutritional supplementation of these products. For example, in a comparison of a control dry food product with that including addition of the calcium salt version of fish oil at a level of up to 4.71%, there has been shown no adverse effect on palatability with dogs, thus affording a source of added nutrition in DHA and EPA and no compromise in flavor. The NBFAM salts may be blended with the pet food components or, in the case of extruded dry and semi-dry products, sprayed or dusted on the surface thereof, with or without components such as palatability enhancers.

The NBFAM salt is added to pet foods and animal foods in general without regard to the protein content which typically varies according to species, breeding status, and age, among other factors. For example, the NBFAM salt may be used with a dry or semi-dry dog food composition for non-breeding, adult dogs, which requires a minimum protein content of about 18% by weight on a dry matter basis. Similarly, the NBFAM salt may be applied to a dry or semi-dry puppy food having a minimum protein content of about 22% by weight on a dry matter basis. The NBFAM salt may also be used with other dry and semi-dry foods of varying protein content, and with foods for other animals such as livestock and research animals.

In accordance with one embodiment of this aspect of the invention, the NBFAM salt is applied to the surface of an extruded dry or semi-dry pet food, usually in the form of pellets or kibbles. The NBFAM salts of the present invention can also be used as an ingredient incorporated in the composition of a dry, semi-dry, or moist pet food product itself. The NBFAM salts used for coating can be applied as a liquid suspension or dry. This will depend on a number of factors including the target animal, the product to be coated, other coating components, and coating equipment to be used.

As referred to within this description, pet foods generally relate to a nutritionally balanced mixture of proteinaceous and farinaceous materials having a moisture content of about 50% or less by weight. Such mixtures are known as dry or semi-dry pet foods to those skilled in the art, and the NBFAM salt is applied to pieces of the dry or semi-dry food. The pet food compositions described herein are not intended to be limited to a specific listing of ingredients because such ingredients will depend on such factors as, for example, the desired nutritional balance for the specific type of pet, and availability of ingredients to the manufacturer. In addition to the proteinaceous and farinaceous materials, the pet food composition may include vitamins, minerals, and other additives such as flavorings, preservatives, emulsifiers and humectants. The nutritional balance, including the relative proportions of vitamins, minerals, fat, protein and carbohydrate, is determined according to dietary standards known in the veterinary art. For example, the nutritional balance of a cat food composition is determined according to the known dietary requirements for cats.

Suitable proteinaceous material may include any material having a protein content of at least about 15% by weight including vegetable proteins such as soybean, cotton seed, and peanut; animal proteins such as casein, albumin, and fresh animal tissue including fresh meat tissue and fresh fish tissue; and dried or rendered meals such as fish meal, poultry meal, meat meal, bone meal and the like. Other types of suitable proteinaceous materials include wheat gluten or corn gluten, and microbial proteins such as yeast.

Suitable farinaceous material may comprise any material having a protein content of less than about 15% by weight and containing a substantial proportion of starches or carbohydrates, including grains such as corn, milo, alfalfa, wheat, barley, rice, soy hulls, and other grains having low protein content. In addition to the proteinaceous and farinaceous materials, other materials such as whey and other dairy by-products, as well as other carbohydrates may be added. In addition, known flavorings including, for example, corn syrup or molasses, may be added.

In one example, the NBFAM salt is applied to a dry cat food composition. Generally, the term cat food composition as used herein applies to commercially sold, nutritionally balanced food compositions that are intended to provide substantially the sole diet for a cat. Thus, such compositions may be described as having a minimum protein content at which cat health is maintained. However, the minimum protein content of the food varies according to the age and breeding status for the animal. For example, a nutritionally balanced cat food composition for breeding females and kittens requires a minimum protein content of at least about 28% by weight on a dry matter basis. A nutritionally balanced cat food composition for non-breeding and adult cats requires a minimum protein content of about 26% by weight on a dry matter basis. More typically, the protein content of commercially available cat food compositions for adult, non-breeding cats is about 30% by weight on a dry matter basis, to insure that the food meets the nutritional requirements of any cat.

For example, a typical formula well known in the art for a dry cat food composition to which the NBFAM salt is applied is as follows:

0%-70% by weight grain-based meal or flour, such as corn, wheat, barley or rice;
0%-30% by weight animal by-product meal, such as poultry or beef meal;
0%-25% by weight corn gluten meal;
0%-25% by weight fresh animal tissue, such as poultry or beef tissue;
0%-25% by weight soybean meal or flour;
0%-25% by weight fresh fish tissue;
0%-20% by weight seafood-based meal;
0%-10% by weight animal fat;
0%-10% by weight high fructose corn syrup;
0%-10% by weight dried molasses;
0%-1.5% by weight phosphoric acid; and
0%-1.5% by weight citric acid.

Additionally, vitamins and minerals are added according to known American Association of Feed Control Officials (AAFCO) guidelines. Such AAFCO Cat Food Nutrient profiles include calcium carbonate, potassium chloride, sodium chloride, choline chloride, taurine, zinc oxide, ferrous sulfate, vitamin E, vitamin A, vitamin $B_{12}$, vitamin $D_3$, riboflavin, niacin, calcium pantothenate, biotin, thiamine mononitrate, copper sulfate, folic acid, and pyroxidine.

Dry pet food may be prepared by a variety of methods. One such method that is widely used on commercial basis is the cooker-extruder method. In the cooker-extruder method, dry ingredients are first blended together to form an admixture. This admixture is transferred into a steam conditioner where it is sufficiently moistened to become extrudable. The admixture then enters a cooker/extruder where it is cooked at an elevated temperature and pressure and then forced out of the apparatus through a die. This die forms the extruded product into a specific shape. Individual pieces of product are created by periodically slicing off the end of the extruded stream of product. The individual pieces, or kibbles, are then dried in a hot air dryer. Generally, the product is dried until it contains less than about 15 percent moisture, and preferably about 9 to 12 percent moisture. The dried particles or pieces are then transferred by bulk conveyor to a coating drum and sprayed with animal fat. Other liquids such as, for example, citric acid or phosphoric acid may alternatively be applied to the pieces, or applied in addition to the animal fat. The resulting pellets or kibbles constitute the basal composition to which a coating of the NBFAM salt is applied.

Coating, as used herein, refers to the topical deposition of the NBFAM salt onto the surface of the basal composition, such as by spraying, dusting, or the like. For example, kibbles of uncoated, extruded basal cat food can be placed in a container such as a tub or coating drum for mixing. A fat, such as lard or tallow, is heated and then sprayed onto the cat food in any convenient manner to obtain a coating of the kibbles. The coating need not be a continuous layer, but preferably is uniform. After the fat cools, the NBFAM salt may be applied as either a dry power or a liquid suspension while the product is mixing. A liquid suspension of the NBFAM salt is typically sprayed on while a dry NBFAM salt is typically dusted on, preferably through a mesh screen to make the application more uniform on the kibbles. Alternatively, a NBFAM salt can be mixed with the fat and applied concurrently. Note that multiple coatings may be applied to achieve uniformity of the coating.

The omega-3 fatty acid monovalent and divalent metal salts of the present invention, and particularly those containing one or more omega-3 fatty acids selected from DHA, EPA, DPA and ALA can be used in the fertility enhancement methods disclosed by U.S. Pat. No. 6,576,667, which is incorporated herein by reference. Applicants have since learned that in addition to DHA and EPA, DPA and LNA also enhance the fertility of ruminants and other animals. The present invention makes possible the preparation of fatty acid monovalent and divalent metal salts with higher levels of omega-3 fatty acids, thereby reducing the quantities that must be fed to obtain the beneficial effect. The present invention therefore includes methods according to that patent using the omega-3 fatty acid monovalent and divalent metal salts of the present invention, including the additionally disclosed omega-3 fatty acid monovalent and divalent metal salts not mentioned in that patent.

The following non-limiting examples set forth herein below illustrate certain aspects of the invention. All parts and percentages are by weight unless otherwise noted, and all temperatures are in degrees Celsius.

EXAMPLES

Example 1

In this example, 300 grams of soy oil was charged to a vessel. The soy oil was then heated to 50° C. After the oil reached 50° C., 45 grams of magnesium hydroxide was added and thoroughly blended. The blend was then heated until the temperature rose to 285° C., at which point the saponification reaction occurred and the temperature rose to 290° C. The reacted material was removed from the vessel and placed in flat pan for cooling. After cooling, the material processed into small granules of a dry, free-flowing magnesium salt.

Example 2

A blend of 50% by weight of fish oil and 50% by weight of tallow was prepared. The blend was then saponified under ambient pressure and atmosphere at a temperature range between about 246° C. to about 260° C. with $Ca(OH)_2$ added at a ratio of 20% by weight of the oil/fat to produce calcium salts. The resulting salts were ground to a free-flowing material, which was then bagged and placed in an environmental chamber. The bagged material was held in the environmental chamber at a temperature ranging from about 41° C. to about 43° C.

None of the stored material developed an elevated temperature, which indicates that no auto-oxidation occurred. The material was then sampled and analyzed with the following results:

| Time (days) | Free Fat | EPA | DHA |
| --- | --- | --- | --- |
| 0 | 1.24% | 5.7% | 6.8% |
| 28 | 0.90% | 5.5% | 6.8% |
| 42 | 1.17% | 5.4% | 6.6% |
| 67 | 2.25% | 5.4% | 6.5% |
| 0 | 2.25% | 4.4% | 5.1% |
| 28 | 2.05% | 4.3% | 5.2% |
| 42 | 0.85% | 4.3% | 5.2% |

Example 3

A blend of 50% by weight of fish oil and 50% by weight of soy oil was prepared and saponified as in Example 2. The salts were then ground to free flowing material, bagged and placed in the environmental chamber as described in Example 2.

None of the stored material developed an elevated temperature, which indicates that no auto-oxidation occurred. The material was then sampled and analyzed with the following results:

| Time (days) | Free Fat | EPA | DHA |
| --- | --- | --- | --- |
| 0 | 2.23% | 4.3% | 5.1% |
| 28 | 0.85% | 4.3% | 5.2% |
| 42 | 2.65% | 4.2% | 5.1% |

Example 4

A blend of 75% by weight of fish oil and 25% by weight of stearin was prepared and saponified as in Example 1. The salts were then ground to free flowing material, bagged and placed in the environmental chamber as described in Example 1.

None of the stored material developed an elevated temperature, which indicates that no auto-oxidation occurred. The material was then sampled and analyzed with the following results:

| Time (days) | Free Fat | EPA | DHA |
| --- | --- | --- | --- |
| 0 | 1.15% | 9.1% | 7.3% |
| 73 | 2.19% | 9.3% | 7.4% |
| 124 | 4.12% | 9.2% | 7.5% |

Example 5

A blend of 50% by weight of fish oil and 50% by weight of stearin was prepared and saponified as in Example 1. The salts were then ground to free flowing material, bagged and placed in the environmental chamber as described in Example 1.

None of the stored material developed an elevated temperature, which indicates that no auto-oxidation occurred. The material was then sampled and analyzed with the following results:

| Time (days) | Free Fat | EPA | DHA |
| --- | --- | --- | --- |
| 0 | 0.95% | 6.8% | 5.4% |
| 90 | 1.52% | 6.7% | 5.3% |
| 129 | 1.57 | 6.4 | 5.1 |

Discussion—Examples 2-5:

The above results, which show no dramatic increase in free fatty acids and no reduction in the levels of EPA and DHA, support the finding that no auto-oxidation has occurred. The lack of temperature rise and no negative changes in the free fatty acid levels nor the EPA and DHA content confirm that no auto-oxidation has occurred. The calcium salts of the blended fish oil/tallow; fish oil/soy oil; and fish oil/stearin are stable.

Figure 3:
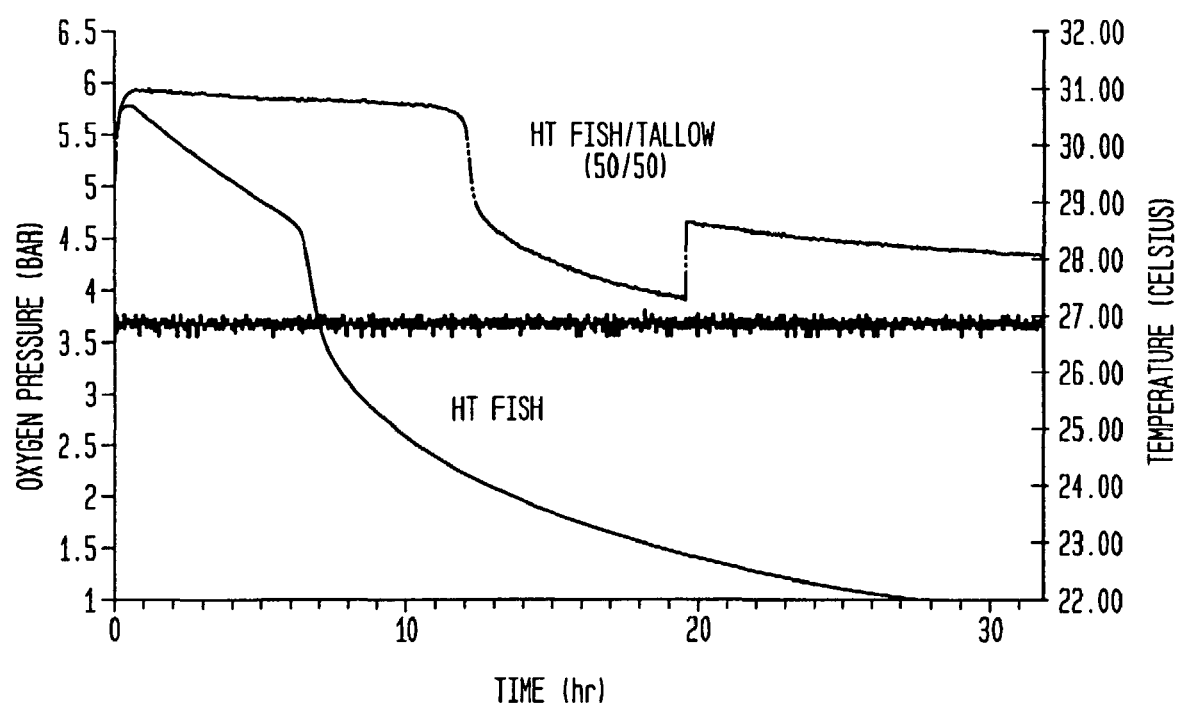
FIG. 3 depicts a comparison of the rates of degradation of a fish oil/tallow metal salt prepared in accordance with a method of the present invention and a fish oil metal salt.

FIG. 3 is a comparison of the rate of degradation of a 50:50 by weight fish oil/tallow metal salt with the rate of degradation of a fish oil metal salt when each metal salt is exposed to an oxygen-rich atmosphere. The 50:50 by weight fish oil/tallow metal salt has a significantly lower rate of degradation than the fish oil metal salt, which confirms that the fish oil/tallow metal salt is more stable in an oxygen-rich environment than a fish oil metal salt that contains no carrier oil.

This should not be interpreted as limiting the scope of the present invention, which provides a means by which beneficial unsaturated fatty acid rich monovalent and divalent metal salts may be prepared having utility as nutritional supplements for essentially any animal for which omega-3 fatty acids provide nutritional or therapeutic benefit.

The foregoing examples and description of the preferred embodiments should be taken as illustrating, rather than as limiting, the present invention as defined by the claims. As will be readily appreciated, numerous combinations of the features set forth above can be utilized without departing from the present invention as set forth in the claims. Such variations are not regarded as a departure from the spirit and scope of the invention, and all such modifications are intended to be included within the scope of the following claims.

What is claimed is:

1. A method for the preparation of a free-flowing, storage-stable fatty acid metal salt product comprising:
    forming a reactive admixture comprising (a) an unsaturated fatty acid glyceride feedstock comprising at least one fatty acid with more than three double bonds; (b) an antioxidant-effective amount of a stabilizing oil to provide an improvement in storage stability; and (c) from about 1 mol to about 3 mol of at least one monovalent metal hydroxide or at least one divalent metal hydroxide; and
    heating the admixture to a temperature at which said fatty acid glycerides saponify to form fatty acid metal salts until a free-flowing, storage-stable product is obtained;
    wherein said stabilizing oil has a fatty acid profile that is more resistant to oxidation than the fatty acid profile of said glyceride feedstock;
    wherein said monovalent metal is potassium; and
    wherein said divalent metal is selected from the group consisting of calcium, copper, magnesium, and zinc.

2. The method of claim 1, wherein the stabilizing oil comprises an oil or a fat comprising an antioxidant-effective amount of fatty acids having 18 or less carbon atoms and 3 or less double bonds.

3. The method of claim 2, wherein the stabilizing oil comprises tallow, soy oil, linseed oil, stearin, or a combination thereof.

4. The method of claim 1, wherein the admixture comprises from about 10 to about 90% by weight of the stabilizing oil.

5. The method of claim 1, wherein the admixture is heated to a temperature at which said fatty acid glycerides saponify to form fatty acid metal salts in an atmosphere in which the partial pressure of oxygen has been reduced by an amount effective to provide a further improvement in storage stability.

6. The method of claim 5, wherein said partial pressure of oxygen is reduced by inert gas blanketing of said admixture while heating.

7. The method of claim 6, wherein said inert gas comprises nitrogen.

8. The method of claim 5, wherein said partial pressure of oxygen is reduced by heating said admixture under vacuum.

9. The method of claim 1, wherein said unsaturated fatty acid glyceride feedstock comprises an unsaturated fatty acid concentration sufficient to form unstable metal salt products when saponified in the absence of a stabilizing oil having antioxidant effects.

10. The method of claim 1, wherein said unsaturated fatty acid glyceride feedstock comprises polyunsaturated fatty acids.

11. The method of claim 10, wherein said glyceride feedstock fatty acids comprise at least one polyunsaturated fatty acid selected from the group consisting of omega-3 and omega-6 fatty acids and combinations of either or both.

12. The method of claim 11, wherein said polyunsaturated fatty acids comprise one or more omega-3 fatty acids selected from the group consisting of DHA, EPA, DPA and ALA.

13. The method of claim 10, wherein said glyceride feedstock fatty acids comprise one or more conjugated fatty acids.

14. The method of claim 13, wherein said one or more conjugated fatty acids comprise one or more CLA isomers.

15. The method of claim 1, wherein said fatty acid glyceride feedstock comprises a mixture of two or more $C_{10}$-$C_{22}$ fatty acids having greater than about 45% by weight of the fatty acid content in the form of fatty acid glycerides.

16. The method of claim 15, wherein about 85 to about 100% by weight of said fatty acid mixture is in the form of fatty acid glycerides.

17. The method of claim 1, wherein said fatty acid glyceride feedstock comprises from about 40 to about 95% by weight of unsaturated fatty acids.

18. The method of claim 1, wherein said feedstock comprises up to about 100% by weight of marine oil.

19. The method of claim 18, wherein said marine oil is selected from the group consisting of menhaden, herring, mackerel, caplin, tilapia, tuna, sardine, pacific saury, krill, kelp, and algae oils.

20. The method of claim 19, wherein said marine oil comprises one or more omega-3 or omega-6 fatty acids selected from the group consisting of DHA, EPA, DPA, ALA, linoleic acid and arachidonic acid.

21. The method of claim 1, further comprising the step of cooling said admixture and forming a solid, free-flowing and granular fatty acid metal salt product.

22. The method of claim 21, wherein said admixture is cooled in said atmosphere in which said partial pressure of oxygen has been reduced by an amount effective to provide an improvement in storage stability.

23. The method of claim 1, wherein said heating step comprises preheating said fatty acid feed stock to a temperature from about 177° C. to about 288° C. and said forming step comprises rapidly forming a uniform homogeneous blend of said fatty acid feedstock and said monovalent metal hydroxide or said divalent metal hydroxide at a rate effective to produce an improvement in storage stability in said metal salt product.

24. The method of claim 1, wherein said mono-valent metal hydroxide or said divalent metal hydroxide is formed in said reactive admixture by combining stoichiometric quantities of a corresponding monovalent metal oxide or divalent metal oxide and water.

25. A fatty acid metal salt prepared by the method of claim 1, wherein said metal salt comprises one or more beneficial unsaturated fatty acids.

26. A fatty acid metal salt according to claim 25, comprising poly-unsaturated fatty acids.

27. The fatty acid metal salt of claim 26, wherein said polyunsaturated fatty acids are selected from the group consisting of omega-3 and omega-6 fatty acids and combinations of either or both.

28. The fatty acid metal salt of claim 27, wherein said polyunsaturated fatty acids comprise one or more omega-3 or omega-6 fatty acids selected from the group consisting of DHA, EPA, DPA, ALA, linoleic acid and arachidonic acid.

29. The fatty acid metal salt of claim 28, comprising at least one polyunsaturated fatty acid selected from the group consisting of about 1 to about 50% by weight DHA, about 1 to about 50% by weight EPA, about 1 to about 25% by weight DPA, about 1 to about 75% by weight ALA, about 0.5 to about 10% by weight arachidonic acid, about 1 to about 80% by weight linoleic acid and about 1 to about 100% by weight CLA.

30. The fatty acid metal salt of claim 26, wherein said polyunsaturated fatty acids comprise one or more conjugated fatty acids.

31. The fatty acid metal salt of claim 30, wherein said one or more conjugated fatty acids comprise one or more CLA isomers.

32. A fatty acid metal salt prepared by the method of claim 18.

33. A fatty acid metal salt prepared by the method of claim 19.

34. A fatty acid metal salt prepared by the method of claim 20.

35. The fatty acid metal salt of claim 34, wherein said marine oil is selected from the group consisting of menhaden, herring, mackerel, caplin, tilapia, tuna, sardine, pacific saury and krill oils.

36. The fatty acid metal salt of claim 34, wherein said marine oil comprises one or more omega-3 or omega-6 fatty acids selected from the group consisting of DHA, EPA, DPA, ALA, linoleic acid and arachidonic acid.

37. A storage-stable metal salt saponification product of an unsaturated oil feedstock consisting essentially of one or more marine oils and an antioxidant-effective amount of a stabilizing oil having fatty acid profile that is more resistant to oxidation than the fatty acid profile of said oil feedstock.

38. The saponification product of claim 37, wherein said one or more marine oils are selected from the group consisting of menhaden, herring, mackerel, caplin, tilapia, tuna, sardine, pacific saury and krill oils.

39. The saponification product of claim 37, wherein said one or more marine oils comprise one or more fatty acids selected from the group consisting of omega-3 and omega-6 fatty acids.

40. The saponification product of claim 39, wherein said one or more marine oils comprise one or more omega-3 or omega-6 fatty acids selected from the group consisting of DHA, EPA, DPA, ALA, linoleic acid and arachidonic acid.

41. The saponification product of claim 40, comprising at least one polyunsaturated fatty acid selected from the group consisting of about 1 to about 25% by weight DHA, about 1 to about 25% by weight EPA, about 1 to about 25% by weight DPA, about 1 to about 75% by weight ALA, about 0.5 to about 10% by weight arachidonic acid, about 1 to about 80% by weight linoleic acid and about 1 to about 80% by weight CLA.

42. A storage-stable fatty acid metal salt saponification product of a fatty acid glyceride feedstock having an unsaturated fatty acid concentration sufficient to form unstable metal salt products when saponified in an ambient atmosphere, further comprising a metal salt of a stabilizing oil having a fatty acid profile that is more resistant to oxidation than the fatty acid profile of said glyceride feedstock.

43. The fatty acid metal salt of claim 42, wherein said unsaturated fatty acid glyceride feedstock comprises polyunsaturated fatty acids.

44. The fatty acid metal salt of claim 43, wherein said polyunsaturated fatty acids are selected from the group consisting of omega-3 and omega-6 fatty acids and combinations of either or both.

45. The fatty acid metal salt of claim 44, wherein said polyunsaturated fatty acids comprise one or more omega-3 or omega-6 fatty acids selected from the group consisting of DHA, EPA, DPA, ALA, linoleic acid and arachidonic acid.

46. The fatty acid metal salt of claim 45, comprising at least one poly-unsaturated fatty acid selected from the group consisting of about 1 to about 50% by weight DHA, about 1 to about 50% by weight EPA, about 1 to about 25% by weight DPA, about 1 to about 75% by weight ALA, about 0.5 to about 10% by weight arachidonic acid, about 1 to about 80% by weight linoleic acid and about 1 to about 100% by weight CLA.

47. The fatty acid metal salt of claim 43, wherein said polyunsaturated fatty acids comprise one or more conjugated fatty acids.

48. The fatty acid metal salt of claim 47, wherein said one or more conjugated fatty acids comprise one or more CLA isomers.

49. The fatty acid metal salt of claim 42, wherein said fatty acid glyceride feedstock comprises from about 50 to about 85% by weight of unsaturated fatty acids.

50. The fatty acid metal salt of claim 42, wherein said stabilizing oil comprises an oil or a fat comprising an antioxidant-effective amount of one or more fatty acids having 18 or less carbon atoms and 3 or less double bonds, and said glyceride feedstock comprises one or more fatty acids having 19 or more carbon atoms and 4 or more double bonds.

51. The fatty acid metal salt of claim 50, wherein the stabilizing oil comprises tallow, soy oil, linseed oil, stearin, or a combination thereof.

52. A method for increasing fertility in an animal, comprising feeding an animal in need thereof an effective amount of a composition of claim 45 comprising at least DHA or EPA.

53. The method of claim 52, wherein said animal is a male or female ruminant.

54. The method of claim 53, wherein said female ruminant is a dairy cow.

55. The method of claim 54, comprising starting the feeding of said product to said ruminant between about 21 days before and about 28 days after parturition.

56. The method of claim 55, wherein said feeding of said product to said ruminant is continued at least until conception occurs.

57. The method of claim 53, wherein said product is fed to said ruminant daily.

58. The method of claim 52, wherein said product is fed to said animal for at least 30 days after conception.

59. The method of claim 58, wherein said product is fed to said animal for at least 60 days after conception.

60. The method of claim 59, wherein said product is fed to said animal for at least 150 days after conception.

61. The method of claim 56, wherein the feeding of said product is discontinued at conception or within 150 days thereafter and said method further includes the step of feeding daily to said ruminant a second fatty acid calcium salt product for supplying milk production energy to a female ruminant after the feeding of the first product is discontinued.

62. A nutritional supplement composition comprising at least one fatty acid metal salt according to claim 25 and a biologically acceptable carrier.

63. A nutritional supplement composition comprising at least one fatty acid metal salt according to claim 38 and a biologically acceptable carrier.

64. A nutritional supplement composition comprising at least one fatty acid metal salt according to claim 42 and a biologically acceptable carrier.

65. The method of claim 1, wherein said reactive admixture comprises a plurality of said metal hydroxides.

66. The fatty acid metal salt product of claim 25 comprising a plurality of metals.

67. The fatty acid metal salt product of claim 38 comprising a plurality of metals.

68. The fatty acid metal salt product of claim 42 comprising a plurality of metals.

69. A food product for a companion animal comprising the fatty acid metal salt product of claim 25.

70. A food product for a companion animal comprising the fatty acid metal salt product of claim 38.

71. A food product for a companion animal comprising the fatty acid metal salt product of claim 42.

72. A food product for human consumption comprising the fatty acid metal salt product of claim 25.

73. A food product for human consumption comprising the fatty acid metal salt product of claim 38.

74. A food product for human consumption comprising the fatty acid metal salt product of claim 42.

75. A nutritionally beneficial fatty acid metal salt comprising an effective amount of the fatty acid metal salt product of claim 25.

76. A method of supplementing the diet of an animal comprising administering to said animal an effective amount of the fatty metal salt product of claim 25.

77. The method of claim 76, wherein said animal is a companion animal.

78. The method of claim 76, wherein said animal is a mammal.

79. The method of claim 78, wherein said mammal is a human.

80. The method of claim 79, wherein said metal salt is a calcium salt.

81. The method of claim 79, wherein said metal salt is a copper salt or a zinc salt.

82. The method of claim 79, wherein said fatty acid is an omega-3 fatty acid or an omega-6 fatty acid.

83. A pet food composition comprising an effective amount of the nutritionally beneficial fatty acid metal salt of claim 75.

84. The pet food composition of claim 83, wherein said nutritionally beneficial fatty acid metal salt is present in an amount sufficient to contribute from about 0.01 to about 5.0 percent by weight to said pet food composition.

85. The pet food composition of claim 83 comprising an extruded dry or semi-dry pet food.

86. The pet food composition of claim 83 comprising a moist pet food.

87. The pet food composition of claim 83, wherein said nutritionally beneficial fatty acid metal salt is added to said pet food composition prior to extrusion.

88. The pet food composition of claim 85, wherein said nutritionally beneficial fatty acid metal salt is dusted thereon in dry form.

* * * * *